(12) United States Patent
Stephan et al.

(10) Patent No.: US 6,362,832 B1
(45) Date of Patent: Mar. 26, 2002

(54) METHOD AND SYSTEM FOR OVERLAYING AT LEAST THREE MICROARRAY IMAGES TO OBTAIN A MULTICOLOR COMPOSITE IMAGE

(75) Inventors: Todd J. Stephan, Santa Clarita; David A. Noblett, Oak Park; Jun Yang, Santa Monica, all of CA (US)

(73) Assignee: Packard BioScience Company, Meriden, CT (US)

( * ) Notice: Subject to any disclaimer, the term of this patent is extended or adjusted under 35 U.S.C. 154(b) by 0 days.

(21) Appl. No.: 09/388,204

(22) Filed: Sep. 1, 1999

(51) Int. Cl.[7] ............................................... G06T 11/60
(52) U.S. Cl. ...................... 345/629; 345/630; 382/128; 382/284
(58) Field of Search ............................... 345/435, 629, 345/632; 382/129, 284

(56) References Cited

U.S. PATENT DOCUMENTS

| | | | |
|---|---|---|---|
| 5,353,056 A | 10/1994 | Westerink et al. | |
| 5,591,981 A | 1/1997 | Heffelfinger et al. | |
| 5,759,781 A | 6/1998 | Ward et al. | |
| 5,814,454 A | 9/1998 | Ju | |
| 6,007,994 A | 12/1999 | Ward et al. | |
| 6,165,734 A | * 12/2000 | Garini et al. | ............... 435/7.21 |
| 6,203,977 B1 | * 3/2001 | Ward et al. | ..................... 435/6 |

FOREIGN PATENT DOCUMENTS

WO    WO 00/2666    5/2000

OTHER PUBLICATIONS

Cheung et al., Analysis of Gene Microarray Images, 06/1999, IEEE, pp. 627–632.*
Blinn, Compositing, Part I: Theory, 09/1994, IEEE, pp. 83–87.*
Brown, A.J., et al., Targeted Display: A New–Technique for the Analysis of Differential Gene Expression, Methods in Enzymology, 1999, vol. 303, pp. 392–408.
Eisen, Michael B., et al., DNA Arrays for Analysis of Gene Expression, Methods in Enzymology, 1999, vol. 303, pp. 179–205.
Zhang, Hong, et al., Differential Screening of Gene Expression Difference Enriched by Differential Display, Nucleic Acids Res., Jun. 1996, vol. 24, No. 12, pp. 2454–2455.
Adryan, B., et al., Digital Image Processing for Rapid Analysis of Differentially Expressed Transcripts on High–Density cDNA Arrays, Biotechniques, Jun. 1999, vol. 6, pp. 1174–1179.
Wadler, S., et al., Quantification of Ribonucleotide Reductase Expression in Wild–Type and Hydroxyurea–Resistant Cell Lines Employing in situ Reverse Transcriptase Polymerase Chain Reaction and a Computerized Image Analysis System, Analytical Biochemistry, Feb. 1999, vol. 267, No. 1, pp. 24–29.
Zhao, N. et al., High Density cDNA Filter Analysis: A Novel Approach For Large Scale, Quantitative Analysis of Gene Expression, Gene, Apr. 1999, vol. 56, No. 2, pp. 207–213.

(List continued on next page.)

*Primary Examiner*—Matthew Luu
*Assistant Examiner*—Motilewa Good-Johnson
(74) *Attorney, Agent, or Firm*—Brooks & Kushman P.C.

(57) ABSTRACT

Method and system for overlaying at least three microarray images to obtain a multicolor composite image, which is then displayed on a monitor of a computer system. The microarray images are taken from a microarray scanner of a DNA microarray and can be viewed simultaneously through the use of the image overlays where each image is represented by a different color. Each pixel of the composite image is generated by the OR operator applied to all corresponding pixels of the microarray images. Registration of the microarray images can be altered with a keyboard or mouse of the computer system.

14 Claims, 2 Drawing Sheets

OTHER PUBLICATIONS

Speicher, et al., "Karyotyping human chromosomes by combinatorial multi–fluor FISH", Nature Genetics, New York, NY, Apr. 1996, pp. 368–375, vol. 12, XPO00930084.

"Adding Colour", Internet Article, Online! XP002163079, Retrieved from the Internet: <URL:http://www.cs.ubc.c/spider/ladic/colour.htm> retrieved on 2001–03–12!

"Microarray Systems", Internet Article, Online! XP002163080, Retrieved from the Internet:<URL:http://www.dssimage.com/microarraySystems.html> retrieved on 2001–03–12!

"Array of Options: Instrumentation to exploit the DNA microarray explosion" THE SCIENTIST, Online! vol. 14, No. 11, May 29, 2000 XP002163081 Retrieved from the Internet: <URL:http//www.the–scientist.com/yr2000/may/profile1_000529.html>retrieved on 2001–03–12! paragraph: "Touched by Light".

"BioChip Arrayer FAQs" INTERNET ARTICLE, Online! XP002163082 Retrieved from the Internet: <URL:http://www.packardbiochip.com/faq/faq.htm> retrieved on 2001–03–12! paragraph 4: "What is the importance of a flexible, multicolor system for microarray analysis?".

* cited by examiner

METHOD AND SYSTEM FOR OVERLAYING AT LEAST THREE MICROARRAY IMAGES TO OBTAIN A MULTICOLOR COMPOSITE IMAGE

TECHNICAL FIELD

This invention relates to methods and systems for overlaying at least three microarray images to obtain a multicolor composite image.

BACKGROUND ART

Spots containing fluorescently labeled DNA samples on a suitable carrier such as a microscope slide or membrane are commonly known as microarrays or bio-chips. An example of a process that uses overlays is in the analysis and quantitation of such microarrays.

The microarrays are typically created with fluorescently labeled DNA samples in a grid pattern consisting of rows 22 and columns 20 typically spread across a 1 by 3 inch glass microscope slide 24, as illustrated in FIG. 1. The rows 22 extend along the smaller dimension of the slide 24 and the columns 20 extend along the larger dimension of the rectangular slide 24. Each spot 26 in the grid pattern (or array) 28 represents a separate DNA sample and constitutes a separate experiment. A plurality of such grid patterns 28 comprises an array set 30. Reference or "target" DNA (or RNA) is spotted onto the glass slide 24 and chemically bonded to its surface. Fluorescently labeled "probe" DNA (or RNA) is then introduced and allowed to hybridize with the target DNA. Excess probe DNA that does not bind is removed from the surface of the slide 24 in a subsequent washing process.

The purpose of the experiment is to measure the binding affinity between the probe and target DNA to determine the likeness of their molecular structures: complementary molecules have a much greater probability of binding than unrelated molecules. The probe DNA is labeled with fluorescent labels that emit light when excited by an external light source of the proper wavelength. The brightness of each sample on the slide 24 is a function of the fluor density in that sample. The fluor density is a function of the binding affinity or likeness of the probe molecule to the target molecule. Therefore, the brightness of each sample can be mapped to the degree of similarity between the probe DNA and the target DNA in that sample. On a typical microarray, up to tens of thousands of experiments can be performed simultaneously on the probe DNA, allowing for a detailed characterization of complex molecules.

Scanning laser fluorescence microscopes or microarray readers as illustrated in FIG. 2 can be used to acquire digital images of the emitted light from a microarray. The digital images are comprised of several thousand to hundreds of millions of pixels that typically range in size from 5 to 50 microns. Each pixel in the digital image is typically represented by a 16 bit integer, allowing for 65,535 different grayscale values. The microarray reader sequentially acquires the pixels from the scanned microarray and writes them into an image file which is stored on a computer hard drive. The microarrays can contain several different fluorescently tagged probe DNA samples at each spot location. The microarray scanner repeatedly scans the entire microarray with a laser of the appropriate wavelength to excite each of the probe DNA samples and store them in their separate image files. The image files are analyzed and subsequently viewed with the aid of a programmed computer.

A typical confocal laser microarray scanner or microarray reader is illustrated in FIG. 2. The reader is commonly used to scan the microarray slide 24 to produce one image for each dye used by sequentially scanning the microarray with a laser of a proper wavelength for the particular dye. Each dye has a known excitation spectra and a known emission spectra. The scanner includes a beam splitter 32 which reflects a laser beam 34 towards an objective lens 36 which, in turn, focuses the beam at the surface of slide 24 to cause fluorescence spherical emission. A portion of the emission travels back through the lens 36 and the beam splitter 32. After traveling through the beam splitter 32, the fluorescence beam is reflected by a mirror 38, travels through an emission filter 40, a focusing detector lens 42 and a central pinhole 44.

Analysis and Quantitation of the Microarray in Two Colors

Analysis of the fluor density at each spot location requires software algorithms that utilize image processing algorithms to locate all the spots and measure the brightness of the pixels in each spot. Visual feedback of the relative spot intensities has commonly been done using software to overlay the two images by encoding the brightness of the image as a function of the brightness of one color for each image, i.e. red or green. When red and green objects are overlayed at the same pixel location, a yellow color is produced as illustrated in FIG. 3.

Given
B1 is the brightness of a pixel in image 1,
B2 is the brightness of a pixel in image 2,
each brightness value is from 0 to 65,535,
Image 1 is to be overlayed in red and an 8 bit pixel will be R1,
Image 2 is to be overlayed in green and an 8 bit pixel will be G1.
R1=B1/256
G1=B2/256

A common method for displaying pixels on a computer monitor or printout is in true color, comprised of 24 bits per pixel, where 8 bits each represent the red, green, and blue color channels, respectively.

$$\text{Pixel } (R, G, B) = R1, G1, 0$$

The visual display of the overlayed images provides the viewer with feedback on the brightness of each spot from each channel of the reader, the relative brightness of each spot to the others by the degree of the color yellow present, and a measure of the spatial registration between images by the amount of red or green on either side of a central yellow color as illustrated in FIG. 3.

The use of two color overlays is common and has been demonstrated by BioDiscovery in a software program called ImaGene and by Stanford University in a software program called ScanAlyze, as well as several places in the literature. Two color visualization has been designed to meet the needs of two color microarray experiments. Two color microarray readers have been designed and built by several companies and are readily available in the market. Microarray readers with more than two colors have just recently been released by the assignee of the present application.

One common use of overlays in microarray experiments and quantitation is to provide visual feedback to scientists of any mis-registration between images. Many microarray readers sequentially scan the microarray with one scan for each DNA probe used. A scan typically starts in the upper left corner of the microarray, usually called the origin, and proceeds in a left to right and top to bottom direction until the entire area has been scanned. When a scan has finished, the scanner mechanically resets the laser to the origin in preparation for the next scan. The difference in the actual position between each image scan is a mis-registration error. By viewing the overlayed image and by zooming the spot features, a scientist can visually quantify the amount of mis-registration between the images.

Another common use of the overlays in microarray experiments is to correct for any mis-registration errors. Typically, the images are presented in a single viewing window with each image assigned a different color. In a two color system, this would typically be green and red. The locations where a match is obtained will be displayed in yellow. The scientist can visually see the areas of green and red on the fringes of a microarray spot and, using a keyboard or mouse, move one image relative to the other until the fringe areas turn yellow. The best registration match will minimize the green and red fringes across the entire microarray pattern.

Articles related to the present invention include the following:

Brown, A. J., et al. "Targeted Display: A New Technique for the Analysis of Differential Gene Expression", METHODS ENZYMOL. 1999; 303:392–408;

Eisen, M. B., et al. "DNA Arrays for Analysis of Gene Expression", METHODS ENZYMOL. 1999; 303:179–205;

Zhang, H., et al. "Differential Screening of Gene Expression Difference Enriched By Differential Display", NUCLEIC ACIDS RES. Jun. 15, 1996;24(12):2454–5;

Adryan, B., et al. "Digital Image Processing For Rapid Analysis of Differentially Expressed Transcripts on High-Density cDNA Arrays", BIOTECHNIQUES. Jun. 26, 1999(6):1174–9;

Wadler, S., et al. "Quantification of Ribonucleotide Reductase Expression in Wild-Type and Hydroxyurea-Resistant Cell Lines Employing In Situ Reverse Transcriptase Polymerase Chain Reaction and a Computerized Image Analysis System", ANAL. BIOCHEM. Feb. 1, 1999;267(1):24–9; and Zhao, N., et al. "cDNA Filter Analysis: A Novel Approach For Large-Scale, Quantitative Analysis of Gene Expression", GENE. Apr. 24, 1995; 156(2):207–13.

SUMMARY OF THE INVENTION

An object of the present invention is to provide a method and system for overlaying at least three microarray images to obtain a multicolor composite image.

In carrying out the above objects and other objects of the present invention, a method is provided for overlaying at least three microarray images to obtain a multicolor composite image. The method includes providing at least three microarray images wherein each of the images includes a plurality of pixels having brightness values. The method also includes assigning each image a different color to obtain colorized images and combining corresponding pixels of each colorized image to obtain overlayed images. The overlayed images form a multicolored composite image. The method also includes the step of displaying the multicolored composite image.

When the overlayed images have a registration, the method may include the step of processing the overlayed images to alter the registration. The step of processing may include the step of receiving a command to move one of the overlayed images relative to the other overlayed images.

The step of providing may include the step of scanning a microarray at at least three different wavelengths to obtain the microarray images.

The step of assigning may include the step of creating a palette having entries for each of the wavelengths to display the microarray images. The entries for each palette are based on a composite color and the brightness values of the pixels of its respective image.

Also, preferably, the step of combining includes the step of logically ORing corresponding pixels of each colorized image.

Still, preferably, the method includes the step of receiving at least one command to select a composite color for each microarray image to be overlayed.

Still further in carrying out the above objects and other objects of the present invention, a system is provided for carrying out each of the above method steps.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

Figure 5:
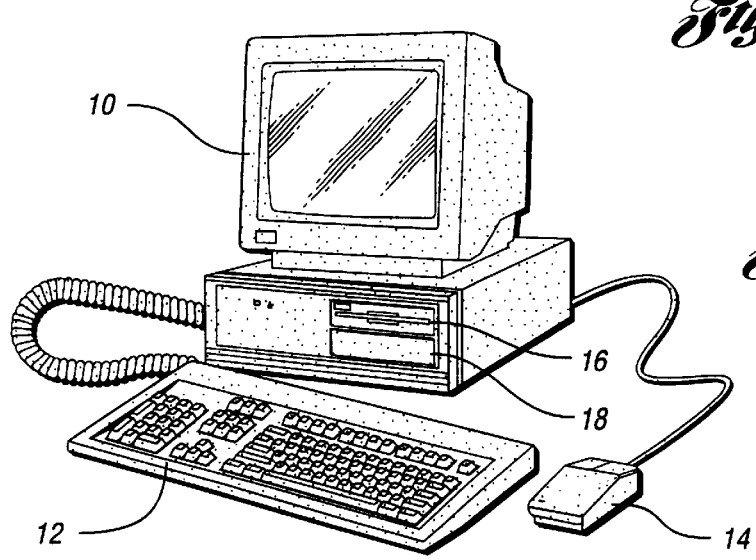
FIG. 5 is a schematic diagram illustrating a preferred hardware configuration on which at least a portion of the method of the present invention can be implemented.

Referring now to the drawing figures, there is illustrated in FIG. 5 a workstation on which the method and system of the present invention can be implemented. However, other configurations are possible. The hardware illustrated in FIG. 5 includes a monitor 10 such as a single SVGA display, a keyboard 12, a pointing device such as a mouse 14, a magnetic storage device 16, and a chassis 18 including a CPU and random access memory. The monitor 10 may be a touch screen monitor used in addition to standard keyboard/mouse interaction. In a preferred embodiment, the chassis 18 is a Pentium-based IBM compatible PC or other PC having at least 32 megabytes of RAM and at least 12 megabytes of hard disk space. The workstation typically includes a Windows NT, graphical user interface as well as an Ethernet 10 Base-T high speed Lan network interface.

Analysis and Quantitation of the Microarray in More Than Two Colors

Software visualization tools are required to meet the needs of the researcher using a reader with more than two scanning laser wavelengths. The design of the overlay software algorithms is not trivial when more than three colors are required due to common practice of representing true color as the compilation of three components, red, green, and blue, each of 8 bits, for a 24 bit color. Natural mathematical properties exist which easily and clearly combine two or even three colors into an overlayed true color image. Overlaying more than three colors is not as visually intuitive.

Microsoft® Windows uses palettes to display all eight bit images. A palette consists of up to 256 values for each of three different colors, red, green, and blue. The intensity of each 8 bit pixel, with a value of 0 to 255, is used to index into the palette. The three values, red, green, and blue, are used to display the pixel in the appropriate color and intensity.

Figure 4:
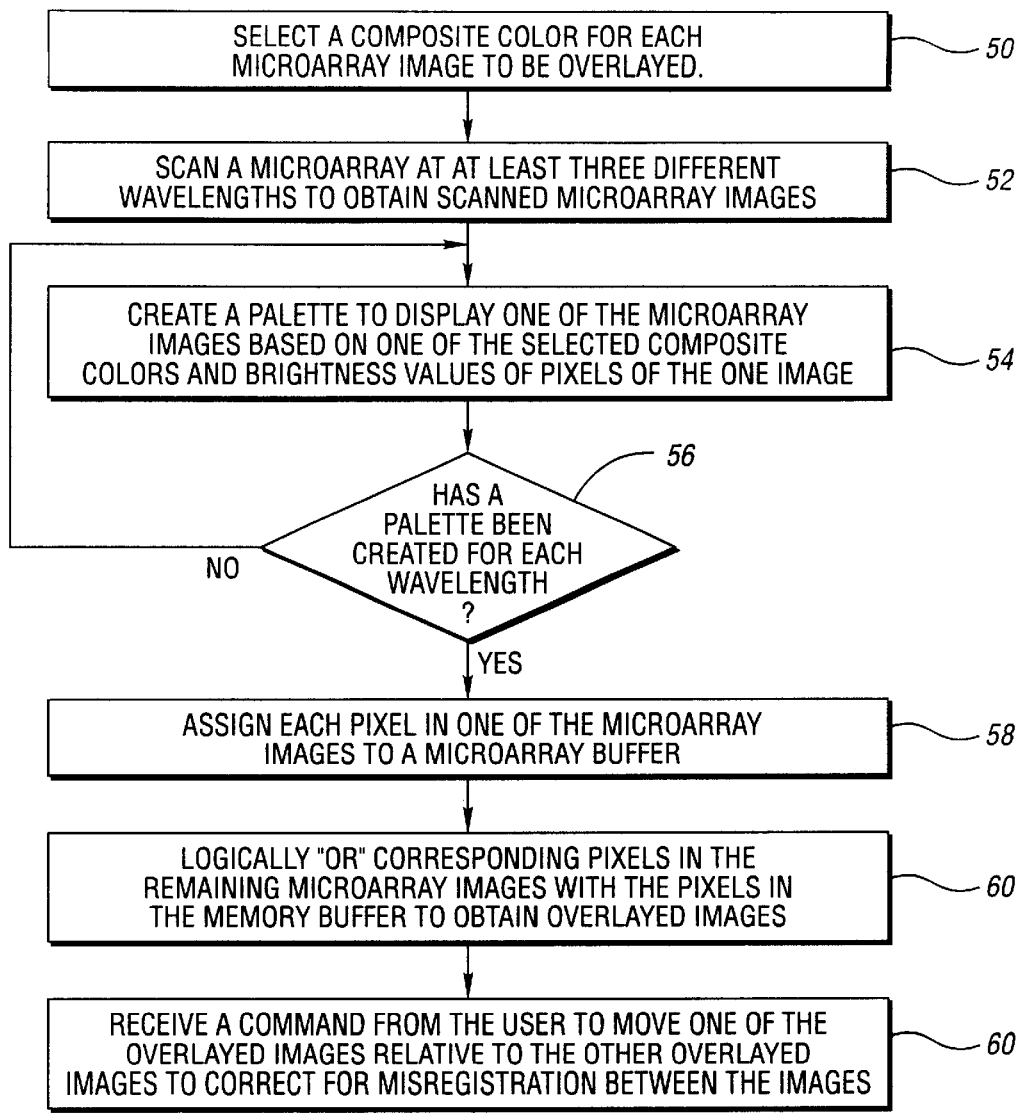
FIG. 4 is a block diagram flow chart illustrating the method of the present invention.

Referring now to FIG. 4, there is indicated in block diagram flow chart form a method for overlaying and then displaying a multicolor composite image from at least three microarray images in accordance with the present invention.

At block 50, typically a user selects a composite color for each microarray image to be overlayed using the workstation of FIG. 5.

Figure 1:
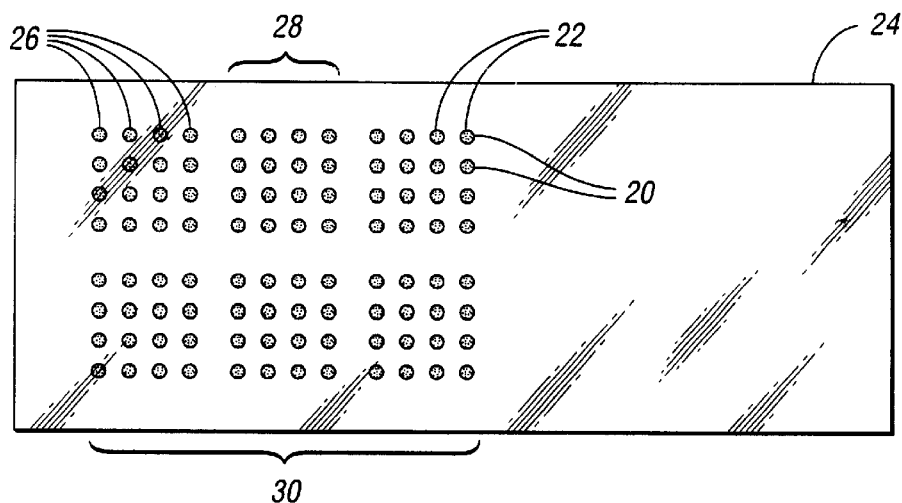
FIG. 1 is a top plan schematic view illustrating a spot, an array and an array set on a glass slide.
Figure 2:
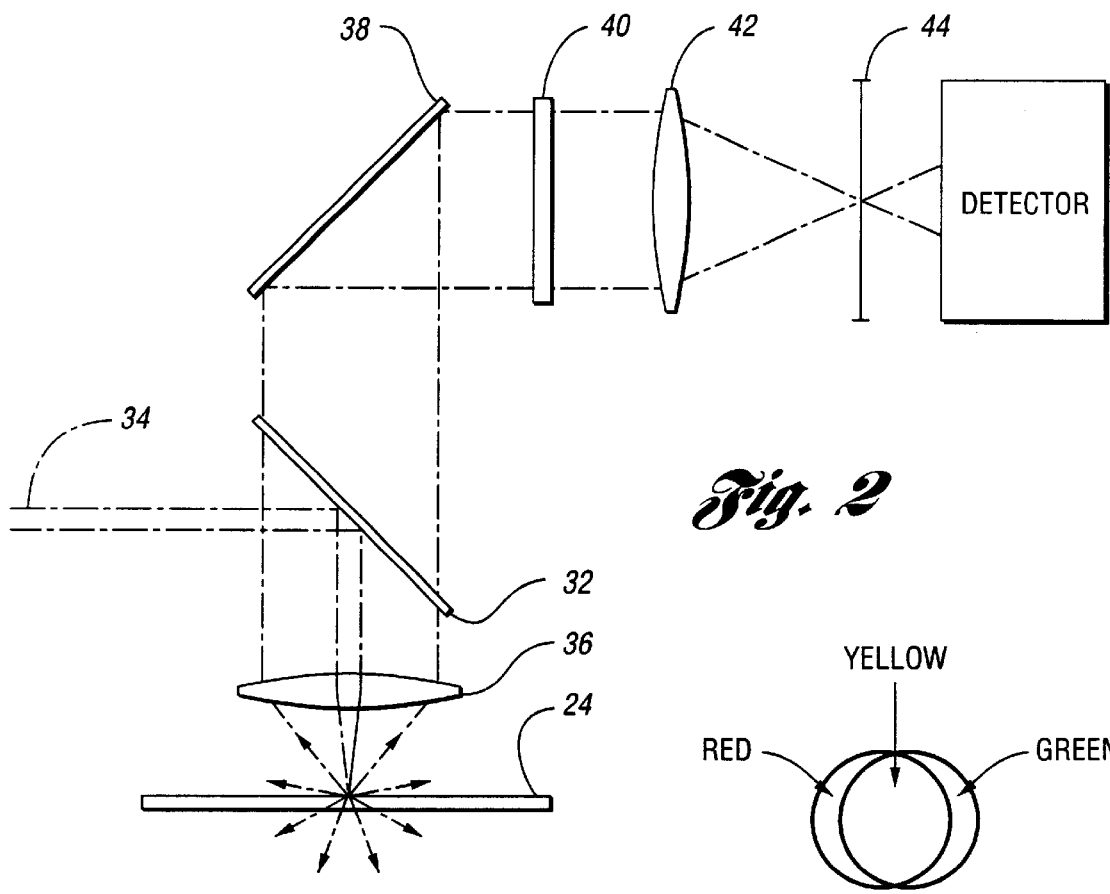
FIG. 2 is a schematic view of a confocal laser reader used to generate digital images.
Figure 3:
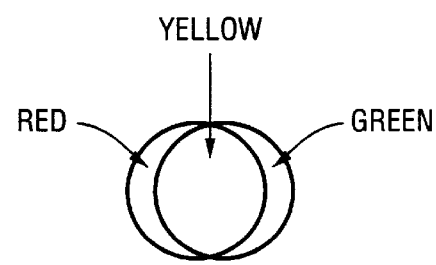
FIG. 3 is a schematic view of overlayed red and green objects with a central yellow color.

At block 52, a microarray is scanned such as by the microarray reader or scanner of FIG. 2 at at least three different wavelengths to obtain scanned microarray images.

For each laser wavelength, at block 54, create a palette based on the user-selected composite color in any combination of red, green and blue values. For example, the user can select the color cyan (R=0, G=255, B=255). That chosen color is assigned to the brightest pixel in the scanned image. In most cases this will be 255. The remaining positions in the palette are successively dimmer representations of the same color. The algorithm of block 54 assigns palette entries for one image based on "NumEntries" palette entries and the chosen color represented by the combination of three components, "red", "green" and "blue". Typical pseudo-code for doing this is as follows:

```
int red=0, green=255, blue=255, NumEntries=256;
PALETTEENTRY pe[256];
for (int i=0 ; i<NumEntries ; i++)
{
    // divide by NumEntries for full spectrum
    pe[i] .peRed=(BYTE) ((float) (i*red)/(float)NumEntries);
    pe[i] .peGreen=(BYTE) ((float) (i*green)/(float)NumEntries);
    pe[i].peBlue=(BYTE) ((float) (i*blue)/(float)NumEntries);
}
pImage->SetPaletteEntries (0, NumEntries, pe);
```

This process is repeated for each image scanned by the laser reader and with a different selected composite color (RGB) as illustrated by block 56.

Now that each image has a palette with its chosen composite color, the images are overlayed. At block 58, for all pixels in a first image, assign each pixel directly to a memory buffer for later drawing or manipulation.

At block 60, for all pixels in the remaining images, logically "OR" each pixel with the corresponding pixel in the buffer.

The following is some exemplary pseudo-code for doing this:

```
for j=0; j<npixels; j++)
{
    buf[j]=image[0] [j];
}
for (i=1; i<nimages-1; i++)
{
    for (j=0; j<npixels; j++)
    {
        buf[j]|=images [i] [j];
    }
}
```

The OR operation used to combine the images is only one of several Boolean operators that can be used to produce varying results. The use of other Boolean operators and combinations of them to produce other effects is included. Other standard Boolean operations for combining images include XOR, NOT and AND.

At block 62, the computer of FIG. 5 receives a command from the user to move one of the overlayed images relative to the other overlayed image to correct for misregistration between the images. This is typically done such as by the keyboard 12 and/or the mouse 14 or other computer interface control.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for overlaying at least three microarray images to obtain a multicolor composite image, the method comprising:

providing at least three microarray images wherein each of the images includes a plurality of pixels having brightness values;

assigning each image a different color to obtain colorized images;

combining corresponding pixels of each colorized image to obtain overlayed images whereby the overlayed images form a multicolor composite image; and displaying the multicolored composite image.

2. The method as claimed in claim 1 wherein the overlayed images have a registration and wherein the method further comprises processing the overlayed images to alter the registration of the overlayed images.

3. The method as claimed in claim 2 wherein the step of processing includes the step of receiving a command to move one of the overlayed images relative to the other overlayed images.

4. The method as claimed in claim 1 wherein the step of providing includes the step of scanning a microarray at at least three different wavelengths to obtain the microarray images.

5. The method as claimed in claim 4 wherein the step of assigning includes the step of creating a palette having entries for each of the wavelengths to display the microarray images, the entries for each palette being based on a composite color and the brightness values of the pixels of its respective image.

6. The method as claimed in claim 1 wherein the step of combining includes the step of logically ORing corresponding pixels of each colorized image.

7. The method as claimed in claim 1 further comprising receiving at least one command to select a composite color for each microarray image to be overlayed.

8. A system for overlaying at least three microarray images to obtain a multicolor composite image, the system comprising:

means for providing at least three microarray images wherein each of the images includes a plurality of pixels having brightness values;

a computer programmed to:
assign each image a different color to obtain colorized images; and
combine corresponding pixels of each colorized image to obtain overlayed images whereby the overlayed images form a multicolor composite image; and a display for displaying the multicolor composite image.

9. The system as claimed in claim 8 wherein the overlayed images have a registration and wherein the computer is further programmed to process the overlayed images to alter the registration of the overlayed images.

10. The system as claimed in claim 9 wherein the computer is programmed to receive a command to move one of the overlayed images relative to the other overlayed images.

11. The system as claimed in claim 8 wherein the means for providing includes a microarray scanner for scanning a microarray at at least three different wavelengths to obtain the microarray images.

12. The system as claimed in claim 11 wherein the computer is programmed to create a palette having entries for each of the wavelengths to display the microarray images, the entries for each palette being based on a composite color and the brightness values of the pixels of its respective image.

13. The system as claimed in claim 8 further comprising a memory buffer and wherein the computer is further programmed to assign each pixel in one of the colorized images to the memory buffer and logically ORing corresponding pixels in the remaining colorized images with the pixels in the memory buffer to obtain the overlayed images.

14. The system as claimed in claim 8 wherein the computer is further programmed to receive at least one command to select a composite color for each microarray image to be overlayed.

* * * * *